United States Patent [19]

Linder et al.

[11] Patent Number: 5,665,067
[45] Date of Patent: Sep. 9, 1997

[54] APPARATUS FOR APPLYING A MULTIPLE-COMPONENT TISSUE ADHESIVE

[75] Inventors: Albert Linder, Leonberg-Hoefingen, Germany; Andreas Kellner, Ulrichskirchen, Austria; Georg Habison; Guenther Zuelow, both of Vienna, Austria

[73] Assignee: Immuno Aktiengesellschaft, Vienna, Austria

[21] Appl. No.: 394,039

[22] Filed: Feb. 24, 1995

[30] Foreign Application Priority Data

Feb. 28, 1994 [AT] Austria ................... 414/94

[51] Int. Cl.[6] ....................... A61M 37/00
[52] U.S. Cl. ................. 604/82; 604/43; 604/191
[58] Field of Search ............. 604/82, 191, 225, 604/53, 54, 275, 283, 43, 287; 222/134, 135, 136; 128/200.21, 200.14

[56] References Cited

U.S. PATENT DOCUMENTS

| | | | |
|---|---|---|---|
| 1,114,268 | 10/1914 | Kells | 604/43 X |
| 1,152,818 | 9/1915 | Kells | 604/43 |
| 3,670,729 | 6/1972 | Bennett et al. | 604/53 |
| 3,753,439 | 8/1973 | Brugarolas et al. | 604/43 |
| 4,037,599 | 7/1977 | Raylerson | 604/283 X |
| 4,040,420 | 8/1977 | Speer | 604/82 |
| 4,179,068 | 12/1979 | Dombrowski . | |
| 4,359,049 | 11/1982 | Redl et al. . | |
| 4,631,055 | 12/1986 | Redl et al. | 604/82 |
| 4,735,616 | 4/1988 | Eibl et al. | 604/191 |
| 4,874,368 | 10/1989 | Miller et al. | 604/82 |
| 4,978,336 | 12/1990 | Capozzi et al. | 604/82 |
| 4,979,942 | 12/1990 | Wolf et al. | 604/83 |
| 5,116,315 | 5/1992 | Capozzi et al. | 604/82 |
| 5,149,330 | 9/1992 | Brightbill | 604/280 |
| 5,474,540 | 12/1995 | Miller et al. | 604/191 |
| 5,582,596 | 12/1996 | Fukunaga et al. | 604/191 |

FOREIGN PATENT DOCUMENTS

| | | |
|---|---|---|
| 379 311 | 12/1985 | Austria . |
| 0 037 393 | 10/1981 | European Pat. Off. . |
| 0 105 493 | 4/1984 | European Pat. Off. . |
| 0 156 098 | 10/1985 | European Pat. Off. . |
| 0 315 222 | 5/1989 | European Pat. Off. . |
| 42 23 356 | 1/1994 | Germany . |

OTHER PUBLICATIONS

"Berijet"®, Behringwerke AG, 1988.
Ogawa et al., "Newly Devised Instrument for Spraying Aeorsolized Fibrin Glue in Thoracoscopic Operations", Ann. Thorac. Surg., 1993, vol. 55, No. 1593–600, pp. 1595–1596.
Linder et al., "A new basic instrumentation for operative thoracoscopy", General Thoracic Surgery, 1993, pp. 42–44, 46–48.

*Primary Examiner*—Corrine M. McDermott
*Assistant Examiner*—V. Alexander
*Attorney, Agent, or Firm*—Foley & Lardner

[57] ABSTRACT

There is disclosed an apparatus for applying a multiple component tissue adhesive, which apparatus has component conveying channels for the components of the tissue adhesive, extending in a one-piece construction part from a connecting part to a delivery part, and a gas conveying channel for a medicinal gas serving for atomizing the tissue adhesive components, wherein all the conveying channels end in separate exit openings at a front side of the delivery part and extend parallel to one another over at least that part of their longitudinal extension which is immediately upstream of the exit openings, and wherein the component conveying channels together are enclosed by the gas conveying channel at least on that part of their longitudinal extension immediately in front of their exit openings.

21 Claims, 3 Drawing Sheets

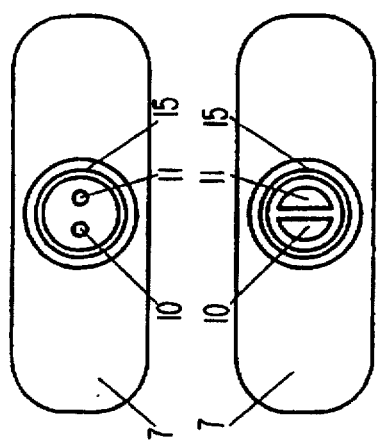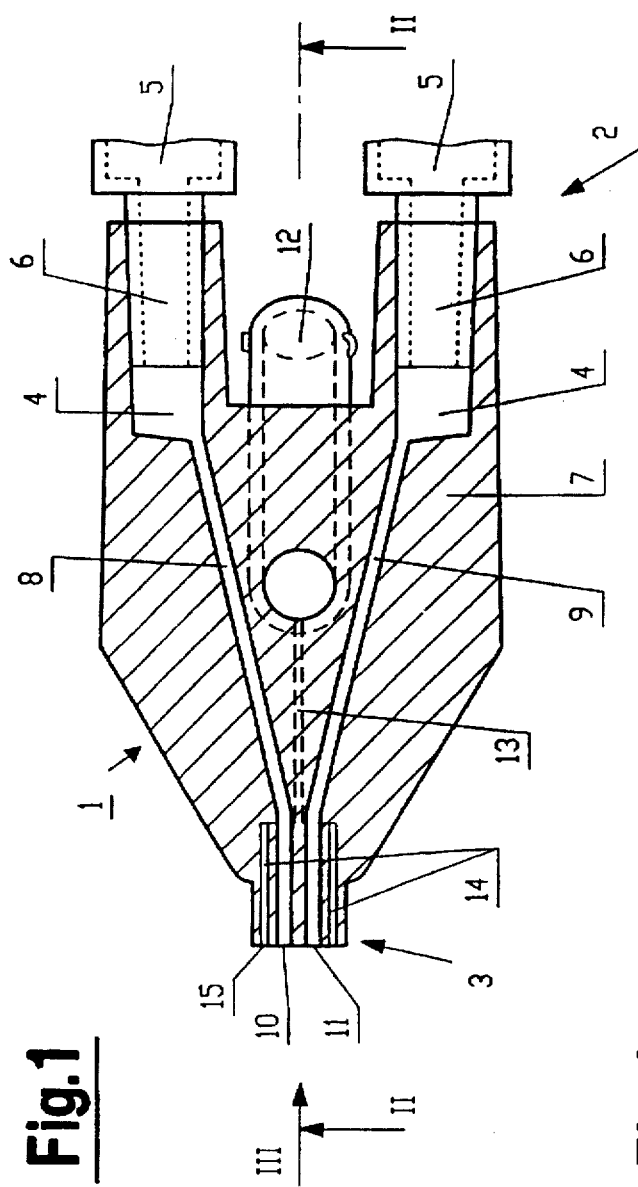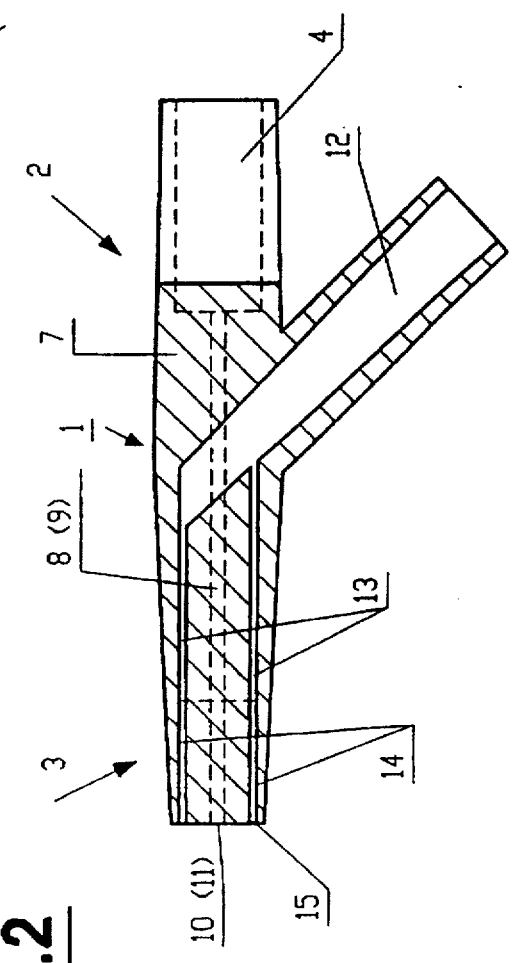

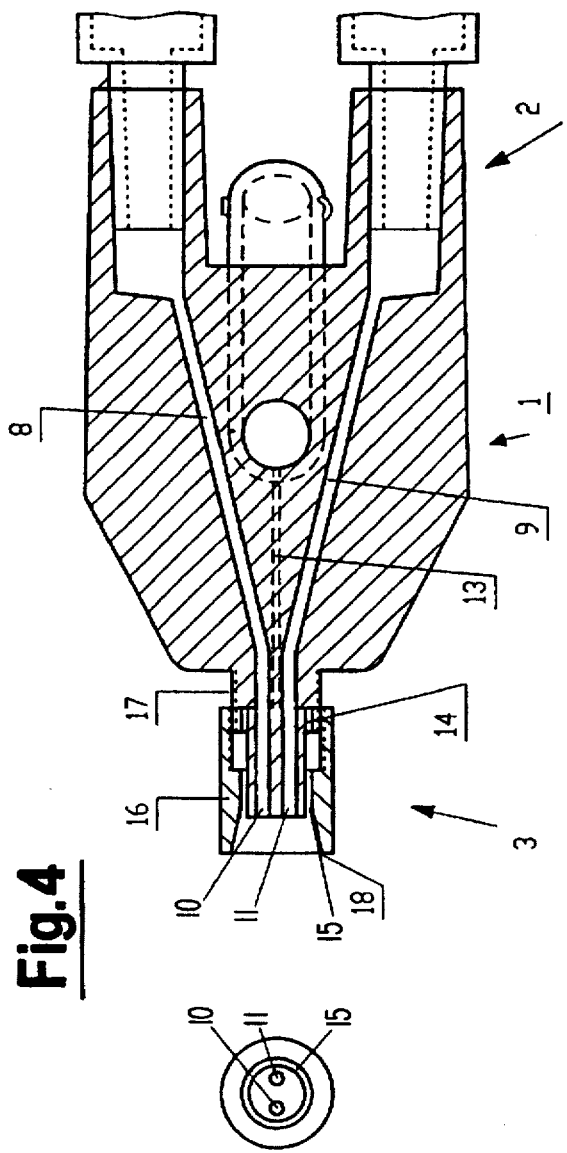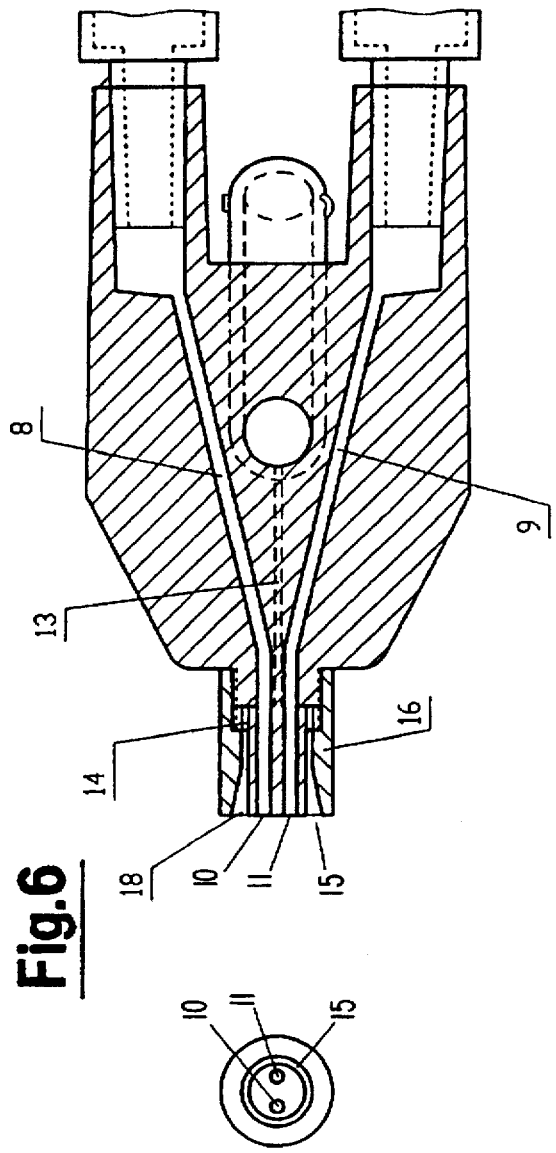

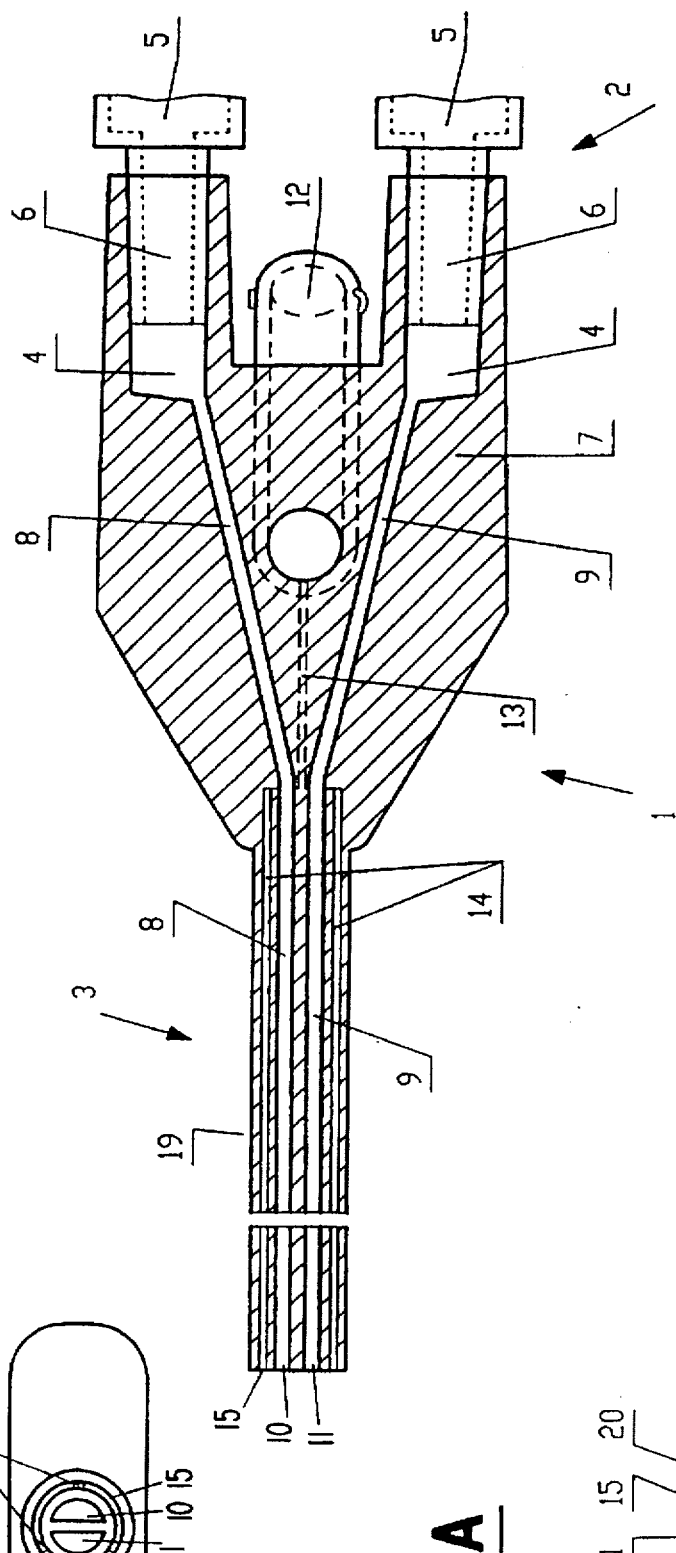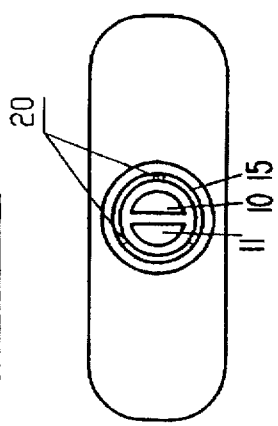

APPARATUS FOR APPLYING A MULTIPLE-COMPONENT TISSUE ADHESIVE

The invention relates to an apparatus for applying a multiple component tissue adhesive, comprising a one-piece structure member having component conveying channels provided for the components of the tissue adhesive and extending through said member from a connecting part to a delivery part, as well as a gas conveying channel for a medicinal gas serving for atomizing the tissue adhesive components, all of the conveying channels ending in separate exit openings at a front side of the delivery part.

A tissue adhesive is mostly provided as a multiple component material which is mixed at application. The reaction of the components (commonly a fibrinogen solution, on the one hand, and a thrombin solution, on the other hand), causes a solidification of the tissue adhesive and thus a desired connection of tissue or organ parts to seal wounds, stop bleedings and the like. For the application of a tissue adhesive it is therefore necessary to store the individual tissue adhesive components strictly separated from one another at first, and then, later on, to mix them and apply them as simultaneously as possible. Application may also comprise the use of a medicinal gas for atomizing a tissue adhesive. By such an atomization, the homogenicity of the mixture shall be guaranteed, on the one hand, and, on the other hand, it is also possible to apply the tissue adhesive on large areas. Particularly preferred fields of application are the stopping of bleedings, the sealing of wounds, burns, skin grafting, and the spraying of body cavities. The resection areas of parenchymatous organs preferably also are treated by spray application. The size of the application area normally is variable by the respective distance of the apparatus from the site of application.

From EP-B 37 393 and the corresponding U.S. Pat. No. 4,359,049, an apparatus for applying a tissue adhesive is known, which may be designed to include a spraying head. The spraying head is also designed as collecting head through which the two tissue adhesive components from individual syringe bodies are guided via separate conveying channels as far as to the exit openings. The spraying head furthermore includes a conveying channel for a sterile gas; this conveying channel is separated into two branches within the head, the exit openings of which are arranged in the region of entry of the component conveying channels. The axes of these exit openings are directed approximately at right angles to the direction of discharge of the two tissue adhesive components. Thus, two separate spray cones are formed, which intersect or unite at a distance from the spraying head, a complete mixing of the sprayed components being possible only as from a certain minimum distance.

An arrangement which is similar in many aspects is sold by Behringwerke AG, of Marburg, Germany, under the name "Berijet"®. There, a flat, one-piece collecting head-spraying head structure member is provided, from which a gas connection part projects at a right angle. In the interior, a gas conveying channel leads from this gas connection part to a front side, and there the gas conveying channel is divided into two separate sub-channels by a separating wall protruding at the front side, which sub-channels end separated from each other at the front side—on either side of the projecting separating wall; a respective conveying channel for one of the two components of the tissue adhesive to be applied enters obliquely into each of these sub-channels in front of their exit openings. Thus, also in that case, two gas jets are formed which, after exiting separately, unite so that the components entrained by them will mix. Yet also there, mixing may be insufficient.

A further apparatus for applying a tissue adhesive is described in AT-B-379 311 or in the corresponding EP-A-156 098 and EP-A-315 222 or U.S. Pat. No. 4,631,055, respectively. Also there, a collecting or spraying head comprises a conveying channel for a medicinal gas, which, closely adjacent and at an acute angle to conveying channels for the two components of a tissue adhesive, leads to the front side of a slip-on projection of the head. Onto this slip-on projection, in particular a separate, fitting multi-lumen catheter is applied such that its lumina are in aligned connection with the conveying channels. Alternatively, a mixing cannula can be applied, in which the individual components are mixed in the gas flow, for which purpose furthermore in particular an inner surface which promotes the turbulence of the components flowing therethrough is provided, which, however, is combined with increased production expenditures.

In Ann Thorac Surg, 55, 1593-600 (1993), pp. 1595-1596, also an apparatus having a separate catheter is disclosed, which enables spraying of a tissue adhesive in thoracoscopic operations. The two components of the tissue adhesive are led via separate syringe bodies to a connecting head, which comprises separate conveying channels for the two components, and to which the catheter is fastened. The catheter consists of a steel tube whose interior is designed such that two disposable plastic tubes, each for one component of the tissue adhesive, can be inserted. The mouths of the plastic tubes project beyond the mouth of the steel tube. The steel tube then has two channels for the components of the tissue adhesive, which each are surrounded by a hollow space passed through by nitrogen gas. The gas is supplied to the catheter via a connection piece provided thereon in the vicinity of the connecting head.

A similar apparatus is described in General Thoracic Surgery, 42–48 (1993) for thoracoscopy. There, too, a steel tube is used, which accommodates a catheter of synthetic material for conveying the two components of the tissue adhesive. The plastic catheter is centered by projections at the distal end of the steel tube. Thus, the plastic catheter is arranged in a hollow space through which a gas is passed. Supply of the gas is also effected directly to the catheter via a corresponding connection piece.

In the two last-mentioned apparatusses including steel tube catheters, it is disadvantageous that the steel tube is provided with the connection means for the medicinal gas, which is inconvenient during surgical applications; a catheter as such should not have any bulky parts in order to avoid injuries.

It is now an object of the invention to provide an apparatus of the initially defined type, which is not only simple to produce and handy to use, but which in particular also guarantees good, homogenous mixing of the components of a tissue adhesive during atomization thereof.

The apparatus according to the invention of the initially defined kind is characterized in that the component conveying channels together are surrounded by the gas conveying channel at least over that part of their longitudinal extension immediately upstream of their exit openings. Preferably, all the conveying channels extend parallel to each other at least over that part of their longitudinal extension immediately upstream of their exit openings.

With such a design, a particularly homogenous mixing of the tissue adhesive components in the spray jet is achieved, it being advantageous that the components emerging through the exit openings of their conveying channels are enclosed on all sides by a single gas jet annularly surrounding them, which entrains the components and swirls them so that they are well mixed. Depending on the geometry of the exit openings on the front side of the apparatus, also an extremely narrow spray jet, or, on the other hand, a diverging spray cone can be obtained, it being suitable in the latter case to design the annular exit opening of the gas conveying channel with a slightly diverging delimiting face at its radial outer side. The present apparatus is also particularly advantageous during its use, handling during the preparatory work for a tissue adhesive application being just as easy and convenient as the spray application of the tissue adhesive itself.

As such, the exit opening of the gas conveying channel as well as the part of this gas conveying channel following thereupon could have any desired closed cross-sectional shape, e.g., the shape of a flat ellipse, yet in the interest of a problem-free handling of the present apparatus, which is independent of any certain orientation during spraying, it has proved to be advantageous if the gas conveying channel, at least over that part of its longitudinal extension which encloses the component conveying channels, is designed as a ring channel of circular cross-section.

A particularly advantageous embodiment of the apparatus according to the invention is characterized in that the exit openings of the component conveying channels are arranged in the plane of the exit opening of the gas conveying channel at the utmost, and preferably they are arranged to be rearwardly offset relative to the same. With such a design, a homogenous mixing of the tissue adhesive components is also safeguarded if the apparatus is held very close to the application site while being used.

To enable variations of the spray cone, it is particularly advantageous if a separate delimiting part outwardly delimiting the gas conveying channel is arranged on the delivery part so as to be longitudinally displaceable in the direction of the conveying channels. In that case, the delimiting part can be displaceably connected with the remaining apparatus via a screw or plug connection, and such displacement enables provision of a small-area, practically punctual, application of the tissue adhesive, or a large-area application of the same, as is required, if a pre-determined distance to the site of application is given. In the interest of a simple design and production, it is suitable, if the delimiting part has the shape of a sleeve. Furthermore, for varying the spray cone, it is advantageous if the inner surface of the delimiting part is divergent, e.g., widens conically, in the region neighbouring the front end side, towards the same.

The present invention furthermore enables integration of a catheter in an advantageous manner so as to allow for an application of the tissue adhesive even at locations which are difficult to reach. Accordingly, another advantageous embodiment of the apparatus according to the invention is characterized in that the delivery part is formed by a multi-lumen catheter formed in one piece with the remaining apparatus, which has a lumen as a conveying channel for each component of the tissue adhesive, and that, furthermore, the multi-lumen catheter comprises a lumen enclosing these component-conveying channels as a gas conveying channel. To safeguard a uniform gas supply and thus a uniform application of the components of the tissue adhesive, it is furthermore advantageous, if the catheter, at least in its region close to the exit openings, comprises radial holding webs within the gas conveying channel lumen, which holding webs keep the conveying channels of the components centered within the enclosing gas conveying channel, and which optionally end at a distance in front of the front end side. Furthermore, the catheter preferably is flexible or plastically pre-shapable, which can be guaranteed by an appropriate material selection for the one-piece construction part forming the present invention; in this case it may further be suitable for the catheter to contain an additional lumen for a shaping wire. By aid of this shaping wire, the catheter can be pre-adjusted to the shape required to effect an application at a body site which is difficult to reach.

In particular, the construction part forming the apparatus, optionally inclusive of the catheter, is made of a synthetic material which guarantees the flexibility of the catheter. Preferably, a flexible catheter has an external diameter of less than 2.5 mm.

The catheter, however, also lends itself to minimal invasive surgical use, if it is enclosed by a rigid sleeve (adapting means) or is itself designed rigidly itself, thereby facilitating the introduction of the catheter into a trocar and thus, e.g., into an abdominal cavity. In particular, the external diameter of a rigid catheter is 4–6 mm, preferably approximately 5 mm, and thus goes well with the internal diameter of a commercially available trocar.

With the present apparatus, the medicinal gas supplied for atomizing or spraying the components of the tissue adhesive is directly supplied into the rear connecting part of the apparatus, wherein the apparatus simultaneously can serve as the connecting piece of syringe bodies. Advantageously, the connecting part for the supply of gas is an obliquely arranged connecting piece, i.e., it extends at an acute angle to the proximal end of the apparatus or at an obtuse angle to the delivery part of the apparatus. This has the advantage that, during use, the gas connecting piece is less impeding to the user. In this context, it has proved to be particularly advantageous if the connecting piece of the gas conveying channel is arranged at an angle of from 120° to 150° to the direction of the conveying channels in the delivery part.

The invention will now be explained in more detail by way of preferred exemplary embodiments illustrated in the drawings, to which, however, it shall not be limited. In detail, FIG. 1 shows a sectioned top view onto an apparatus for applying a tissue adhesive;

FIG. 2 shows a longitudinal section through this apparatus, along line II—II of FIG. 1;

FIG. 3 shows a front view of this apparatus, according to the arrow III of FIG. 1;

FIG. 3A shows an embodiment of the apparatus in a view similar to that of FIG. 3, yet slightly modified relative to the same;

FIG. 4 shows a modified embodiment of the apparatus according to the invention which, at least at present, is particularly preferred, in a sectional representation similar to FIG. 1, and having a longitudinally displaceable, sleeve-shaped delimiting part for adjustment of the spray cone delivered;

FIG. 5 is a pertaining front view of the delivery part of this apparatus according to FIG. 4;

FIGS. 6 and 7 show this apparatus with the delimiting part in a different position for obtaining a different spray cone adjustment, in illustrations similar to those of FIGS. 4 and 5;

FIG. 8 shows a further embodiment of the apparatus according to the invention with an integrated spraying catheter, in a partially interrupted cross-sectional representation similar to FIGS. 1, 4 and 6;

FIG. 9 shows a pertaining front view of this apparatus, similar to the illustration of FIG. 3; and FIG. 9A shows an illustration of an embodiment that is slightly modified relative to FIG. 9 and has an additional lumen in the catheter part of the apparatus to receive a shaping wire, in a comparable front view.

All the embodiments of the present apparatus which are illustrated in the drawings have a one-piece construction member 1, in particular of synthetic material, including a connecting part 2 for the supply of components of a tissue adhesive (usually a fibrinogen solution and a thrombin solution), as well as for the supply of a medicinal gas used for atomization (usually sterile compressed air, nitrogen or carbon dioxide), and a delivery part 3. For supplying the components of the tissue adhesive, the connecting part 2 comprises two plug-in coni 4 (preferably Luer coni), to which disposable syringe bodies 5, which contain the adhesive components, are connected by aid of appropriately designed connecting coni 6. In the interior of a collecting head 7 of the apparatus, the plug-in coni 4 are continued as component conveying channels 8, 9, which lead from these plug-in coni 4 to front-side exit openings 10, 11 in the delivery part 3. The component conveying channels 8, 9 for guiding the tissue adhesive components in this case may have circular cross-sections, as is illustrated in FIG. 3, or semi-circular cross-sections, as is apparent from FIG. 3A, this being so at least in the delivery part 3 close to the front side provided with the exit openings 10, 11.

Furthermore, on the lower side of the collecting head 7, which substantially is formed by the flat, generally plate-shaped construction member 1 and simultaneously forms a spraying head in the embodiment according to FIGS. 1 to 5, a connection piece 12 for a medicinal gas, e.g., nitrogen, sterile compressed air or carbon dioxide, is arranged in the connecting part 2, in particular at an obtuse angle of from 120° to 150° relative to the longitudinal plane of the collecting head 7 at the delivery side. One or several gas conveying channel(s) 13 lead from this gas connection piece 12 towards the front side of the spraying head 7, merging into an annularly closed channel 14 with preferably circular-ring-shaped exit openings 15 (cf. FIG. 3, FIG. 3a) in the delivery part 3. The annular gas conveying channel part 14 thus annularly encloses the component conveying channels 8, 9 in the region of their exit openings 10, 11, as is particularly clearly visible by the various front views in the accompanying drawings, e.g. in FIGS. 3, 3A, and also in FIGS. 5, 7 as well as in FIGS. 9 and 9A. Thus, in the delivery part 3, all channels 8, 9 and 14 extend in parallel.

When during operation a gas flow is released via the connection piece 12 and the one or several conveying channels 13, 14 to the exit opening 15, the two tissue adhesive components, which are supplied to the component conveying channels 8, 9 by pressing on the syringe pistons, and which emerge at the exit openings 10, 11, are entrained by the gas flow emerging at the exit opening 15 and are atomized in a spray cone while being mixed well.

The embodiment according to FIGS. 4 to 7 largely corresponds to that according to FIGS. 1 to 3, except for an adjustable exit opening for the medicinal gas, and thus, the description of these embodiments in the following shall substantially be limited to, the differences relative to the embodiment according FIGS. 1 to 3.

In detail, the component conveying channels 8, 9 end at the front side, in the manner previously described, in the exit openings 10, 11, which, again, may, e.g., have circular cross-sections. In contrast to the embodiment according to FIGS. 1 to 3, however, the annular gas conveying part 14 following upon the gas conveying channel 13 is now delimited by a separate, sleeve-shaped, longitudinally displaceably arranged external wall delimiting part 16, instead of a rigid external wall portion of the delivery part 3. This delimiting part 16 may, e.g., be screwed or displaceably slipped onto a cylindrical projection piece 17 of the construction member 1, for which purpose an appropriate external or internal thread or appropriate latching knobs or the like (not illustrated), which prevent the delimiting part 16 from falling off, may be provided. In FIGS. 4 and 6, the outer and inner threads provided for a screw connection are schematically indicated.

The inner surface of the sleeve-shaped delimiting part 16 has a conically widening shape at its front part neighbouring the front side, as is illustrated at 18 in FIG. 4. By axially displacing the sleeve-shaped delimiting part 16, thus, the spreading angle of the spray cone can be varied, on account of a variation of the exit openings 15 of the gas conveying channel 13, 14 immediately surrounding the exit openings 10, 11 of the component conveying channels 8, 9. Thus, in the position according to FIG. 4, in which the delimiting part 16 has been forwardly displaced in the longitudinal direction as far as possible, a narrow exit opening 15 and thus a narrow spray cone is obtained. In the position according to FIG. 6, the delimiting part 16 has been rearwardly displaced as far as possible, thus forming a wide exit opening 15 for the gas and thus making it possible to obtain a wide spray cone. In intermediate positions of the delimiting part 16, corresponding intermediate adjustments of the spray cone are obtained.

In respect of its collecting head 7, the embodiment of the apparatus illustrated in FIGS. 8 and 9 also largely corresponds to the embodiments hitherto described, so that also in this case a new description thereof is not necessary. Yet, with the embodiment according to FIGS. 8 and 9, the various conveying channels 8, 9 (for the components of the tissue adhesive) as well as 13 (for the medicinal gas) are continued in corresponding channels in a multi-lumen catheter 19 made in one piece with the collecting head 7, which catheter forms the delivery part 3 in this instance. Within the annular gas conveying channel 14 (compressed air gap), approximately radially extending holding webs 20 are provided, which maintain the ring shape of the channel 14 in the catheter 19, i.e., which keep the inner catheter part comprising the component conveying channels 8, 9 centered. These webs 20 end shortly in front of the exit openings 10, 11, 15, so that the gas outlet on the front side of the catheter 19 may again be continuously ring-shaped, in particular circular.

By an appropriate material selection of the construction part 1 forming the apparatus (collecting head 7 inclusive of catheter 19), the catheter 19 may be designed to be either rigid or flexible.

If the catheter 19 is made to be flexible, it preferably has a diameter of less than 2.5 mm, and furthermore, as illustrated in FIG. 9A, it may contain an additional lumen 21 for a shaping wire 22. Thus, the flexible catheter 19 may be brought into any desired shape which it will keep thereafter.

If the embodiment including the catheter 19 is provided for use in minimal invasive surgery, the catheter tube 19 preferably is made rigid, and an external diameter of 5 mm is chosen; for this purpose, the catheter 19 may also be inserted by aid of an adapter tube (not illustrated) of suitable diameter slipped thereover, via an access instrument.

Although the invention has been explained above in more detail by way of particularly preferred exemplary embodiments, it is self-evident that further changes and modifications are possible within the scope of the invention. Thus, e.g., also in the embodiment comprising the integrated catheter 19 according to FIGS. 8 and 9, it is conceivable to provide component conveying channels 8, 9 of circular cross-section having corresponding circular exit openings 10, 11, similar to those illustrated in FIGS. 3 or 5. On the other hand, in the embodiment according to FIGS. 4 and 6 comprising the longitudinally displaceable delimiting sleeve 16 for adjustment of the spray cone, it is, of course, also conceivable to design the exit openings 10, 11, and the parts of the component conveying channels 8, 9 following thereupon, with a generally semicircular cross-section, similar to those illustrated in FIGS. 3A or 9. The construction part 1 forming the apparatus (collecting head/spraying head 7 or spraying head 7 inclusive of catheter 19, respectively) is preferably made of a common synthetic material used in the medical field, such as, e.g., a polyolefin (polyethylene, polypropylene), polyurethane, PVC or ABS (acrylonitrile butadiene styrene), by injection molding or by extrusion. Similarly, also the sleeve-shaped delimiting part 16 may, of course, also be made of such a synthetic material.

What we claim is:

1. An apparatus for applying a multiple component tissue adhesive, comprising a one-piece construction member having a connecting part and a delivery part, a respective component conveying channel for each of the components of said tissue adhesive, as well as a gas conveying channel for a medicinal gas intended for atomizing said components of said tissue adhesive, said component and gas conveying channels extending from said connecting part to said delivery part and ending in separate exit openings and ending with a front end of said delivery part, wherein said component conveying channels are enclosed by said gas conveying channel at least over a portion of their longitudinal extension directly upstream of said respective exit openings.

2. An apparatus as set forth in claim 1, wherein said component conveying channels and said gas conveying channel extend in parallel at least over a portion of their longitudinal extension immediately upstream of said respective exit openings.

3. An apparatus as set forth in claim 1, wherein said gas conveying channel, at least over the portion of its longitudinal extension enclosing said component conveying channels, is designed as an annular channel having a circular cross section.

4. An apparatus as set forth in claim 1, wherein said separate exit openings of said component conveying channels at most are arranged in a plane defined by said exit opening of said gas conveying channel.

5. An apparatus as set forth in claim 1, wherein said separate exit openings of said component conveying channel are arranged rearwardly offset to a plane defined by said exit opening of said gas conveying channel.

6. An apparatus as set forth in claim 1, further comprising a separate delimiting part outwardly delimiting said gas conveying channel and arranged on the delivery part so as to be longitudinally displaceable in the direction of said conveying channels.

7. An apparatus as set forth in claim 6, wherein said delimiting part is sleeve-shaped.

8. An apparatus as set forth in claim 6, wherein said delimiting part has an internal surface, said internal surface widening towards its front end side in a region neighbouring said front end side.

9. An apparatus as set forth in claim 8, wherein said internal surface widens conically.

10. An apparatus as set forth in claim 1, wherein said delivery part is formed by a multi-lumen catheter formed in one piece with the remaining apparatus, said catheter including one respective lumen for each one of said component conveying channels, and including a further lumen enclosing said component conveying channels to constitute said gas conveying channel.

11. An apparatus as set forth in claim 10, further comprising radial holding webs contained within said further lumen provided at least in the region close to said exit openings, said holding webs maintaining said component conveying channels in centered relationship within said enclosing gas conveying channel.

12. An apparatus as set forth in claim 11, wherein said holding webs terminate at a distance upstream of the front end side.

13. An apparatus as set forth in claim 10, wherein said catheter is flexible.

14. An apparatus as set forth in claim 13, wherein said catheter has an external diameter of less than 2.5 mm.

15. An apparatus as set forth in claim 10, wherein said catheter is capable of being pre-shaped.

16. An apparatus as set forth in claim 15, wherein said catheter further contains an additional lumen to accommodate a shaping wire.

17. An apparatus as set forth in claim 10, wherein said catheter is rigid.

18. An apparatus as set forth in claim 17, wherein said catheter has an external diameter of from 4 mm to 6 mm.

19. An apparatus as set forth in claim 17, wherein said catheter has an external diameter of 5 mm.

20. An apparatus as set forth in claim 1, wherein said connecting part for said gas conveying channel is a connection piece arranged at an obtuse angle relative to said delivery part.

21. An apparatus as set forth in claim 20, wherein said connection piece of said gas conveying channel is arranged at an angle of from 120° to 150° relative to the direction of said component conveying channels in said delivery part.

* * * * *